(12) United States Patent
Alonso et al.

(10) Patent No.: US 6,693,082 B2
(45) Date of Patent: Feb. 17, 2004

(54) METHOD OF INHIBITING METASTATIC DISSEMINATION USING DESMOPRESSIN

(75) Inventors: Daniel Fernando Alonso, Ranelagh (AR); Daniel Eduardo Gomez, Bernal (AR); Guillermo Skilton, Quilmes (AR); Eduardo Francisco Fariias, Buenos Aires (AR); Elisa Dora Bal de Kier Joffé, Buenos Aires (AR)

(73) Assignee: Universidad Nacional de Quilmes, Bernal (AR)

( * ) Notice: Subject to any disclaimer, the term of this patent is extended or adjusted under 35 U.S.C. 154(b) by 0 days.

(21) Appl. No.: 09/875,671

(22) Filed: Jun. 5, 2001

(65) Prior Publication Data

US 2002/0013262 A1 Jan. 31, 2002

Related U.S. Application Data

(62) Division of application No. 09/510,405, filed on Feb. 22, 2000, now abandoned.

(30) Foreign Application Priority Data

Feb. 23, 1999 (AR) .................................... P 99 01 00736

(51) Int. Cl.$^7$ ............................................... A61K 38/11
(52) U.S. Cl. .......................... 514/16; 424/198.1; 514/2
(58) Field of Search .......................... 424/78.08, 198.1; 514/16, 2

(56) References Cited

PUBLICATIONS

Ono, et al., 1992, ACTA Neurochirugica, 114(1–2):26–32.*
Gurney, et al. 1989, European J of Surg Oncol, 15:282–284.*

* cited by examiner

*Primary Examiner*—Anthony C. Caputa
*Assistant Examiner*—Misook Yu
(74) *Attorney, Agent, or Firm*—Hughes Hubbard & Reed LLP; Ronald Abramson; Peter A. Sullivan

(57) ABSTRACT

The present invention relates to the use of 1-deamino-8-D-arginine vasopressin (desmopressin), or a pharmaceutically acceptable salt thereof or a pharmaceutical composition containing any of them, in the preparation of a medication which minimizes metastatic dissemination during cancer surgery. Additionally, the invention also relates to pharmaceutical compositions comprising the same and to a method of treating a mammal in order to inhibit metastatic spread during surgical extirpation of a cancer mass.

9 Claims, 2 Drawing Sheets

METHOD OF INHIBITING METASTATIC DISSEMINATION USING DESMOPRESSIN

The present application is a division of our pending application Ser. No. 09/510,405 filed Feb. 22, 2000, now abandoned, entitled "PHARMACOLOGICAL COMPOUND COMPRISING DESMOPRESSIN, ITS PHARMACOLOGICAL PREPARATION, AND ITS ADMINISTRATION TO INHIBIT METASTATIC DISSEMINATION DURING CANCER SURGERY," which claims priority under 35 U.S.C. §119 to previously filed Argentine application Ser. No. P99 01 00736, filed Feb. 23, 1999.

The present invention relates to a method of treating a mammal in order to inhibit metastatic spread in surgical extirpation of a cancer mass, using 1-deamino-8-D-arginine vasopressin (desmopressin).

BACKGROUND OF THE INVENTION

In spite of the continuous advances in surgical techniques and of the development of adjuvant intensive therapeutics to treat neoplastic diseases, the vast majority of deaths caused by cancer is related to metastatic dissemination.

European Patent Publication EP 380370 discloses local recurrence inhibition of a tumor surgical resection of the application of high molecular weight polymer having extracellular matrix modulators, saccharides, and synthetic peptides, for example:

```
Gly Arg Gly Asp Ser      SEQ. ID. NO. 1
1             5
```

Wound irrigations to prevent tumor local recidives on the surgical wound are disclosed; there is no mention therein about a preventive action against distant metastases.

As is well known in the art, metastases are lesions arising from a cancer mass, which have no contiguity relationship with the tumor from which they originate. The process by which malignant cells leave their primary site to disseminate throughout the body has become one of the main goals of cancer research with broad applications of great significance from a medical viewpoint.

The capacity to produce metastases is an attribute that distinguishes malignant neoplastic cells from benign tumor cells; malignant neoplastic cells can be released from the primary tumor and survive a complex series of interactions with the normal tissues and cells of the host, finally settling on a distant site. The overall phenomenon is triggered when cancer cells invade and occupy adjacent tissues, penetrating into body cavities and into circulation.

U.S. Pat. No. 4,588,587 (EP 263608) discloses metastasis inhibition in mammals by the administration of a natural protein extract with anti-coagulating and anti-proteolytic properties, obtained from the leech salivary gland. This extract would block tumor cell passage from circulation into other anatomic compartments. As this is a scarcely characterized natural extract, there is no defined pharmacological data available and no accurate process has been proposed to prevent the occurrence of metastatic spread during cancer surgery. Furthermore, its enhanced anticoagulant activity limits the application thereof during surgical manipulation because of the eventual risk of severe bleeding.

The process of invasion and metastasis via the blood stream includes a series of sequential stages which gave rise to the concept of a "cascade" phenomenon. The different steps follow a certain order and they are vital for a cancer cell to disseminate towards possible target organs (I. J. Fidler, Cancer Metastasis. Br. Med Bull. 1991, 47:157–77). First, the development and organization of new blood vessels on the increasing tumor mass take place. Then, cancer cells adhere to the new vessel walls, destroying their supportive matrix architecture and gaining access to the circulatory stream (P. Mignatti, D. B. Rifkin, Biology and Biochemistry of Proteinases in Tumor Invasion, Physiol. Rev. 1993, 73:161–95). Tumor cells are then passively carried to secondary implantation sites. Finally, they stop and become adhered to the vascular endothelium, they extravasate and start their proliferation again to form a metastatic focus.

While metastatic and tumoral invasion determine, in the end, the biological aggressiveness and the progression of the disease, most conventional therapeutic strategies are based on proliferation inhibition or on the destruction of neoplastic cells, and not on the reduction of the invasive or the metastatic properties thereof. In order to achieve a therapeutical action through the use of chemical agents or radiotherapy, it is necessary for the patient to undergo dosages that elicit clinical symptoms of toxicity. Unfortunately, this toxic action is not restricted to the growing tumor cell population and also affects fast renewing normal tissues, as well as epithelia and hematopoietic tissue.

Thus, the creation of new treatment strategies based on the interruption of metastatic dissemination is crucial.

Tumor cell spread towards circulation during surgical manipulation of a neoplastic mass was confirmed in experimental animal models and the implications of these results for the surgery of patients affected with cancer was broadly discussed for a long time from an empirical viewpoint.

Recently, the presence of circulating tumor cells in blood samples taken from the veins of patients subjected to breast cancer surgery was studied by Reverse Transcription and Polymerase Chain Reaction (RT-PCR) (D. C. Brown, A. D. Purushotham, G. D. Birnie, W. D. George, Detection of Intraoperative Tumor Cell Dissemination in Patients With Breast Cancer Using Reverse Transcription and Polymerase Chain Reaction. Surgery 1995, 117:95–101). This methodology, based on the specific mammary markers DF3 y CK 8, achieved sensitivity to detect 10 tumor cells in 5 ml of blood. The results confirmed the presence of cancer cells in blood during the surgical act with cells progressively disappearing from circulation.

These observations confirm for the first time the need to have adjuvant therapeutical strategies to minimize metastatic dissemination during the surgical manipulation of solid neoplasms.

During hematogenous metastasis, the tumor cell embolus must survive transportation into the blood stream, to become adhered later to a blood vessel and invade its wall. The vast majority of tumor cells are rapidly eliminated in the circulation, even if the aggregation of cells together, with blood platelets, or the formation of a fibrin network in the embolus, increase the chances of survival (V. Constantini, L. R. Zacharski, The Role of Fibrin in Tumor Metastasis, Cancer Metastasis Rev. 1992, 11:283–90; L. Weiss, F. W. Orr, K. V. Honn, Interactions of Cancer Cells With the Microvasculature During Metastasis, FASEB J. 1988, 2:12–21).

Publication WO 9217492, discloses new RGD (Arg-Gly-Asp) or KGD (Lys-Gly-Asp) peptides which inhibit platelet aggregation and adhesion-molecule receptors, suggesting the potential usefulness thereof in atherosclerosis, coronary, disease, phlebitis or cancer. The reference to the use in cancer is rare and is oriented to the reversion of coagulation disorders associated to the disease rather than limiting metastases.

Recently, we have examined the effects of different, neuropeptidic hormones and synthetic derivatives thereof on our mammary carcinoma murine model F3II (D. F. Alonso, G. Skilton, H. G. Farina, M. S. De Lorenzo, D. E. Gomez, Modulation of Growth and Urokinase Secretion by Vasopressin and Closely Related Nonapeptides in Metastatic Mouse Mammary Tumor Cells. Int. J. Oncol. 1997, 10:375–79). We have reported that vasopressin and its synthetic analog, desmopressin, significantly affect the behavior of these neoplastic cells in culture in vitro. It was found that in concentrations within a physiological range (100 ng/ml at 1 μg/ml), these peptides are able to modulate breast cancer cell proliferation and urokinase secretion, a plasminogen-activating enzyme with profibrinolytic activity, involved in the metastasis via the hemal route.

In addition, according to Gader et al., desmopressin stimulates endothelial release of fibrinolytic system effectors, including the plasminogen tissue activator, the urokinase, and the specific inhibitor PAI-1 (A. M. A. Gader, J. Da Costa, J. D. Cash, A New Vasopressin Analogue and Fibrinolysis, Lancet 1973, ii: 1417–18). The activation of the plasminogen in plasmin generates the lysis of circulating fibrin clots. This fibrinolysis activation becomes complemented by the hemostatic effect of desmopressin, which effect is linked to an increase of plasmatic levels of coagulation factor VIII and of the von Willebrand factor (P. M. Mannucci, M. Aberg, I. M. Nilsson, B. Robertson, Mechanism of Plasminogen Activator and Factor VIII Increase After Vasoactive Drugs, Br. J. Haematol. 1975, 30:81–93).

1-Deamino-8-D-arginine-vasopressin, also referred to as desmopressin, is a synthetic analog of the antidiuretic hormone, vasopressin. The antidiuretic hormone (ADH) vasopressin is released by the posterior hypophysis or neurohypophysis. It performs an important role in the regulation of urine concentration and in the maintenance of body fluids. In addition, it can regulate blood circulation by means of its potent vasopressor effect.

Vasopressin is a nine amino acid peptide closely related in structure to another neurohypophysis hormone, oxytocin. The structure of vasopressin is well preserved, as it is identical in all mammals:

SEQ. ID. NO. 2
Cys Tyr Phe Glu Asp Cys Pro Arg GlyNH$_2$
1           5 pigs being the exception where the arginine in the -8 position is replaced by lysine. Cysteine residues form a disulfide bridge between the -1 and the -6 position, which is essential for the biological activity of all these nonapeptides (V. du Vigneaud, D. T. Gish, P. G. Katsoyannis, A Synthetic Preparation Possessing Biological Properties Associated With Arginine Vasopressin. J. Am. Chem. Soc. 1954, 76:4751–52).

A synthetic analog of vasopressin, that is 1-deamino-8-D-vasopressin: S—CH$_2$—CH$_2$—CO—Tyr—Phe—Gln—Asn—Cys—Pro—DArg—GlyNH$_2$, the so-called desmopressin, was prepared for the first time by the end of the 1960s (M. Zaoral, J. Kole, F. Sorm, Amino Acids and Peptides, LXXI, Synthesis of 1-Deamino-8-D-Aminobutyrine-Vasopressin, 1-Deamino-8-D-Lysine-Vasopressin, and 1-Deamino-8-D-Arginine-Vasopressin, Coll. Czech. Chem. Commun. 1967, 32:1250–57). Deamination in the -1 position provides the molecule with enhanced resistance to peptidase degradation; the inclusion of D-arginine in the -8 position reduces its pressor effect and strengthens its antidiuretic action.

Desmopressin possesses a much longer half-life and pharmacological action in vivo than the naturally occurring peptide. These properties make desmopressin the preferred agent in the treatment of diabetes insipidus, which disease is due to an inadequate hypophysial secretion of vasopressin.

BRIEF SUMMARY OF THE INVENTION

In view of the modulator properties of desmopressin on the behavior of tumor cells and the action thereof on the circulating fibrinolytic system, in accordance with the prior art previously described, the Applicants have researched the ability of desmopressin to alter the metastatic cascade in an animal model of solid tumor metastatic dissemination. The model reproduces the massive release of cancer cells into the circulating stream which could take place during surgical manipulation of a neoplastic mass.

The results obtained unexpectedly show for the first time the inhibition of lung metastatic colonization by mammary tumor cells through the application of desmopressin, making possible the availability of a medication useful to minimize metastatic dissemination during breast cancer surgery.

However, this action might be exerted on any other malignant solid tumor with metastatic potential disseminating in blood circulation. In particular, those carcinomas and adenocarcinomas originating from organs capable of inducing peritumoral fibrin deposition and which are subject to intravascular transportation.

It is an object of the present invention to use 1-deamino-8-D-arginine vasopressin (desmopressin) or a pharmaceutically acceptable salt thereof or a pharmaceutical composition containing any of them, in the preparation of a medication which inhibits metastatic dissemination in a second organ by metastatic tumor cells spread during the surgery of a cancerous tumor in a first organ.

Preferably, it is an object of the invention to use 1-deamino-8-D-arginine vasopressin (desmopressin) or a pharmaceutically acceptable salt thereof or a pharmaceutical composition containing any of these, in the preparation of a medication which inhibits metastatic dissemination in lungs by metastatic cells disseminated during breast cancer surgery.

It is still another object of the invention to provide a pharmaceutical composition which inhibits metastatic dissemination in a second organ by metastatic tumor cells spread during the surgery of a cancerous tumor in a first organ, comprising 1-deamino-8-D-arginine vasopressin (desmopressin) or a pharmaceutically acceptable salt thereof, together with a pharmaceutically acceptable carrier or diluent.

Preferably, it is an object of the present invention to prepare a pharmaceutical composition which inhibits lung metastatic dissemination by metastatic tumor cells spread during the surgery of a cancerous breast tumor, comprising 1-deamino-8-D-arginine vasopressin (desmopressin) or a pharmaceutically acceptable salt thereof, together with a pharmaceutically acceptable carrier or diluent.

It is also an object of the present invention to prepare a pharmaceutical composition which inhibits metastatic dissemination in a second organ by metastatic tumor cells spread during the surgery of a cancerous tumor in a first organ, comprising the formulation of 1-deamino-8-D-arginine vasopressin (desmopressin) or a pharmaceutically acceptable salt thereof, together with a pharmaceutically acceptable carrier or diluent.

Another object of the present invention is to prepare a pharmaceutical composition which inhibits lung metastatic dissemination by metastatic tumor cells spread during the surgery of a cancerous breast tumor, comprising the formulation of 1-deamino-8-D-arginine vasopressin (desmopressin) or a pharmaceutically acceptable salt thereof, together with a pharmaceutically acceptable carrier or diluent.

Furthermore, another object of the present invention is a method to inhibit mammal metastatic dissemination in a second organ by metastatic tumor cells spread during the surgery of a cancerous tumor in a first organ, comprising the administration by injection of a therapeutically effective amount of 1-deamino-8-D arginine vasopressin (desmopressin) or a pharmaceutically acceptable salt thereof to the mammal, together with a pharmaceutical composition containing any of those.

Even more preferably, the object of the present invention is based on a method to inhibit lung metastatic dissemination in mammals by metastatic tumor cells spread during the surgery of breast cancer, comprising the administration by injection,of a therapeutically effective amount of 1-deamino-8-D arginine vasopressin (desmopressin) or a pharmaceutically acceptable salt thereof to the mammal, together with a pharmaceutical composition containing any of those.

1-Deamino-9-D-arginine vasopressin (desmopressin) can be preferably used in the form of a pharmaceutically acceptable salt. For the purpose of the present invention, desmopressin acetate is preferably used.

DETAILED DESCRIPTION OF THE PREFERRED EMBODIMENTS

Figure 1:
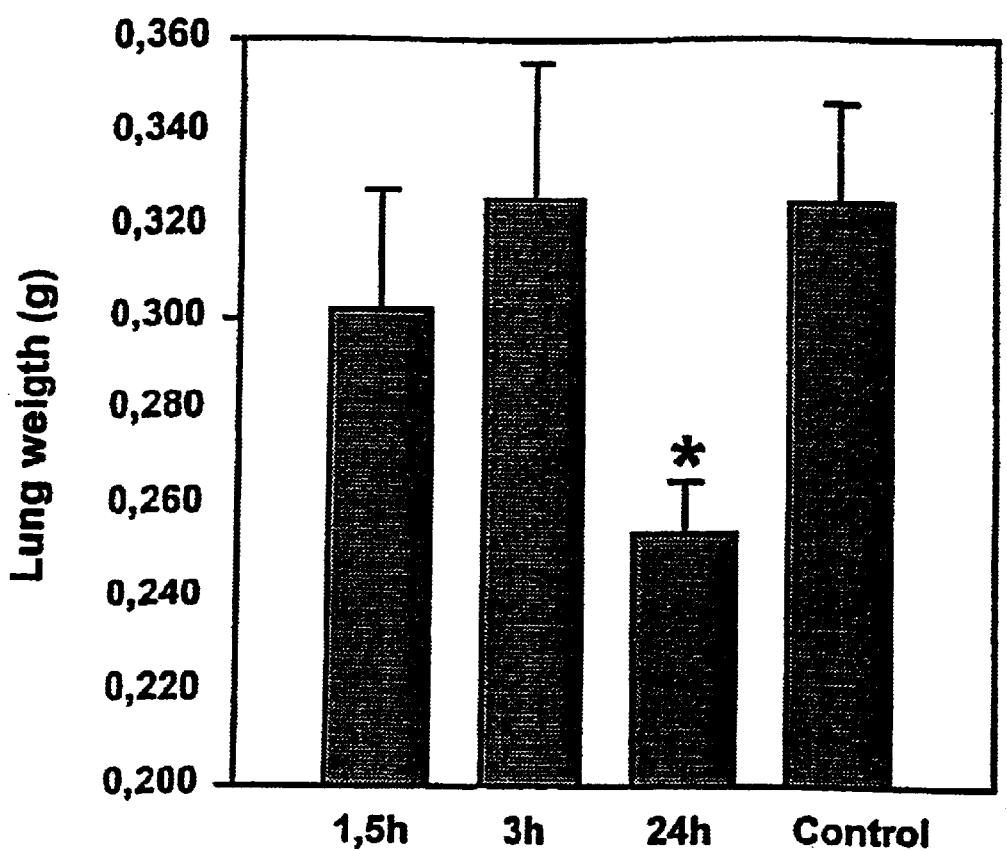
FIG. 1 is a bar chart showing lung weight versus time of inoculation in accordance with the experimental results of Assay 2 as described below.

The ability of desmopressin to alter the metastatic cascade in an animal model of solid tumor metastatic dissemination was determined by experiments herein explained below.

Assay 1: Inhibition of Metastatic Colonization by the Application of Desmopressin 12–16 weeks old syngenic mice from the BALB/c strain weighing 25 g on average were used.

As tumor cells, murine mammary cancer cell lines F3II (sarcomatoid carcinoma) and LM3 (poorly differentiated adenocarcinoma) were used and kept in monolayer culture in minimum essential medium (MEM, Gibco, Grand Island, N.Y.), supplemented with 5% heat-inactivated bovine fetal serum, 2 mM glutamine and gentamicine 80 µg/ml (D. F. Alonso, E. F. Farías, A. Urtreger, V. Ladeda, M. C. Vidal, E. Bal de Kier Joffé, Characterization of F3II, a Mammary Sarcomatoid Carcinoma Cell Line Originated From a Mouse Adenocarcinoma, J. Surg. Oncol. 1996, 62:288–97). In order to collect them, cells were trypsinized following conventional procedures.

Desmopressin available from Ferring Pharmaceuticals (Malmo, Sweden) was used. Desmopressin as provided by Sigma Chemical Co. (St. Louis, Miss.) was also employed.

Mice were inoculated with tumor cells at a concentration of $2 \times 10^5$ cells/0.3 ml MEM/mouse in the side vein of their tails, in accordance with the following schedule and using eight animals in each group:

Coinjection with Desmopressin: tumor cells were preincubated in serum-free MEM and i.v. coinjected with desmopressin, at a final dose of 1 µg (F3II cells) or 2 µg (LM3 cells) per kg of body weight.

Preincubation with Desmopressin: tumor cell suspensions were preincubated in serum-free MEM for 30–60 minutes at 37° C., in the presence of equivalent concentrations of desmopressin (80–160 ng/ml MEM). Then, cells were pelleted, resuspended in serum-free MEM and i.v. injected in the absence of desmopressin.

Control: animals inoculated with tumor cells, with no desmopressin treatment.

Three weeks after inoculation, lung weights were quantified and the number of pulmonary metastatic nodules was determined under the dissection microscope. Results are shown in Table 1.

TABLE 1

| Treatment | Number of median pulmonary nodules (range) | |
| --- | --- | --- |
| | F3II Cells | LM3 Cells |
| Control | 14 (5–36) | 10 (1–33) |
| Coinjection with desmopressin | 5 (0–12)* | 3 (1–18)* |
| Preincubation with desmopressin | 19 (3–66) | 12 (8–37) |

* p < 0.01, Kruskal-Wallis test.

No variations in the metastatic properties dependent on the sex of the animals were seen in any tumor cell lines.

Coinjection with desmopressin at the time of the intravenous inoculation both in tumor cells F3II and in LM3 significantly inhibited the formation of experimental pulmonary metastases. In both cases, the number of metastatic nodules decreased about 70% in animals treated with desmopressin.

Tumor cell preincubation in vitro with equivalent concentrations of desmopressin, however, did not lessen the incidence of metastatic nodules, evidence which excludes the possibility that desmopressin has a direct antimetastatic effect.

Assay 2: Extension of Desmopressin Action on Experimental Metastases

Four groups of ten mice each were organized, and were inoculated with breast carcinoma tumor cells F3II, in accordance with the above description for Assay 1. Thereafter they were intravenously injected with desmopressin in 0.1 ml of physiological solution at different times (1.5 hours, 3 hours and 24 hours) after the inoculation with tumor cells.

Quantification of pulmonary weights took place three weeks after tumoral inoculation. The results are depicted in FIG. 1, in which they are expressed as media±error standard. Similar results were obtained by quantifying the number of pulmonary metastatic nodules per animal.

As shown in FIG. 1, the inhibition of metastases was also effected by the i.v. administration of desmopressin 24 hours after the inoculation of tumor cells. No extrapulmonary metastases were found in any control animal or animal treated with desmopressin.

Assay 3: Cell Survival and Cytotoxicity In Vitro

A. F3II tumor cell suspensions were incubated at 37° C. in serum-free MEM:

in the absence of desmopressin, in the presence of desmopressin, at concentrations of 80 ng/ml, in the presence of desmopressin, at concentrations of 160 ng/ml.

Figure 2:
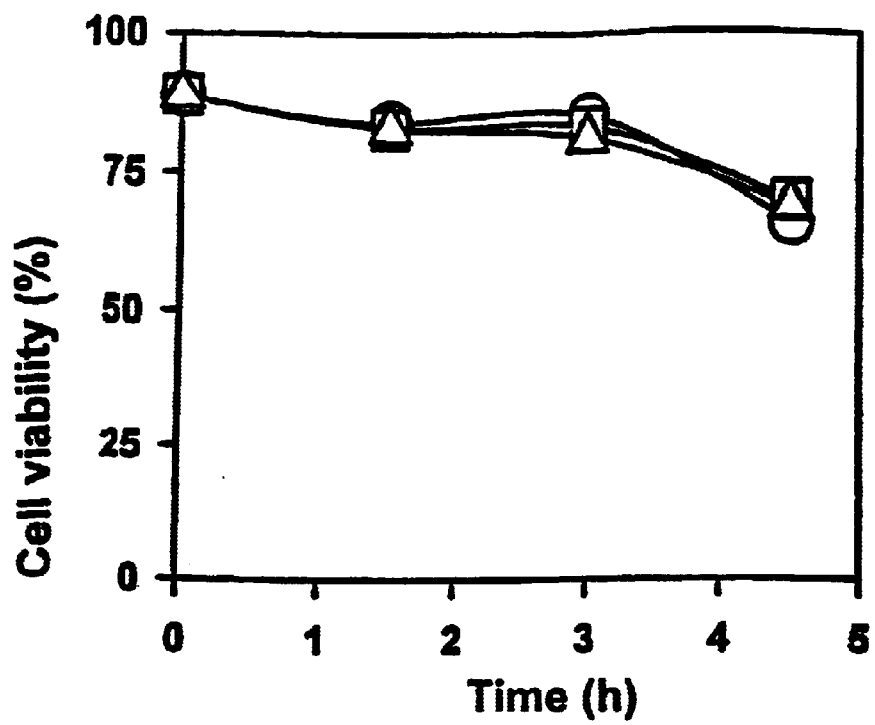
FIG. 2 is a graph of cell viability versus time in accordance with the experimental results of Assay 3 as described below.

After 1–5 hours, cellular viability was assessed by the trypan blue technique. The results are shown in FIG. 2, where the absence of desmopressin (squares) and the presence of desmopressin are represented at concentrations of 80 ng/ml (triangles) and of 160 ng/ml (circles). As seen, desmopressin did not reduce cell viability of tumor cell suspensions.

B. The effect of desmopressin was assayed on semi-confluent tumor monolayers in serum-free MEM cultured in vitro for 24–48 hours, at a concentration of 80 ng/ml and of 160 ng/ml. Monolayers were washed, fixed, and stained with toluidine blue and solubilized with 1% SDS. The number of cells was estimated from the absorbance at 595 nm.

Figure 3:
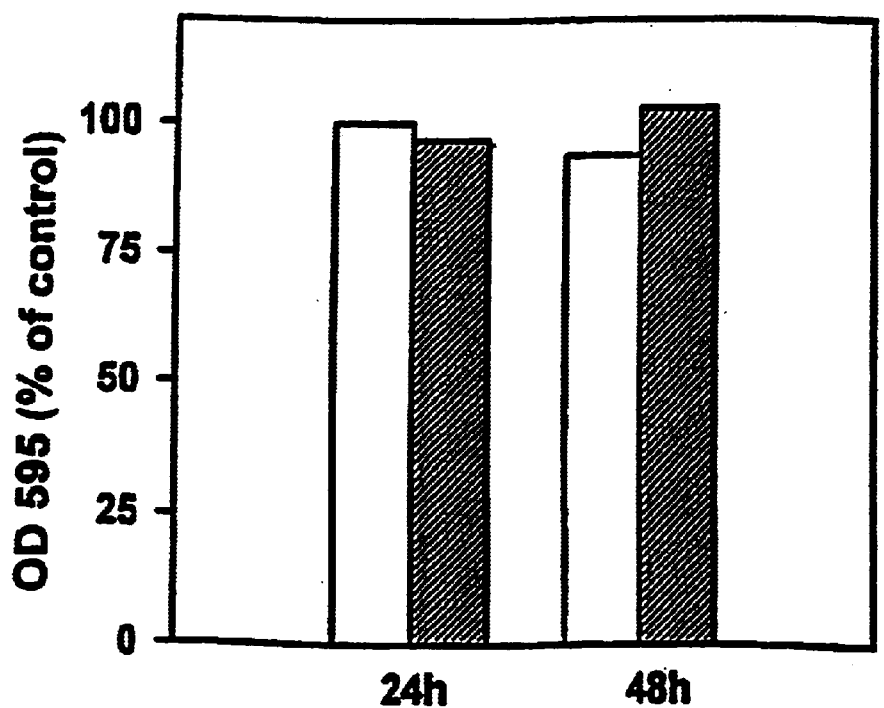
FIG. 3 is a bar chart showing the effect of desmopressin in vitro in accordance with the experimental results of Assay 3 as described below.

The results are shown in FIG. 3, where desmopressin concentrations of 80 ng/ml (light bars) and of 160 ng/ml (dark bars) are represented. In all events, the standard deviation was less than 10%. It follows that semi-confluent tumor monolayers were not affected by the 24–48 hour incubation in the presence of desmopressin, whereby the absence of direct cytotoxic properties of desmopressin is evidenced.

These pre-clinical assays demonstrate for the first time the inhibition of lung metastatic colonization by mammary tumor cells through the application of desmopressin, the synthetic derivative of the vasopressin hormone. Future research could confirm the precise biological action mechanism by which desmopressin develops its effects on distant metastases. However, it is clear that the action of desmopressin takes place at the early stages of the metastatic colonization process, most likely limiting the formation of the tumor cell embolus, as well as altering the interactions of cancer cells with the vascular endothelium in the target organ.

The likelihood that antimetastatic properties of DESMOPRESSIN are associated to direct antitumoral effects was dismissed, taking into account that in vitro tumor cell preincubation in the presence of desmopressin did not modify its ability to produce metastatic colonies in the lung (Assay 1). Furthermore, desmopressin did not decrease the viability of tumor cell suspensions or monolayers in culture (Assay 3). This data disregards a cytotoxic phenomenon as a mechanism of antimetastatic action of the peptide and suggest, on the contrary, the modulation of a biological process in the host.

Metastatic cells entering circulation interact with the effector elements of blood coagulation. This interaction results in fibrin deposition around tumor cells, which determines the formation of a microthrombus that enhances the efficiency of metastasis process (V. Constantini, L. R. Zacharski, The Role of Fibrin in Tumor Metastasis, Cancer Metastasis Rev. 1992, 11:283–90; N. Esumi, D. Fan, I. J. Fidler, Inhibition of Murine Melanoma Experimental Metastasis by Recombinant Desulfatohirudine, a Highly Specific Thrombin Inhibitor, Cancer Res. 1991, 51:4549–56). Fibrin deposition causes a major aggregation of tumor cells together and favors the entrapment thereof in the target organ microvasculature; it also protects tumor cells from destruction by the immune system (Y. Gunji, E. Gorelik, Role of Fibrin Coagulation in Protection of Murine Tumor Cells from Destruction by Cytotoxic Cells, Cancer Res. 1988, 48:5216–21). In this sense, we have previously reported an increase in metastatic colonization of breast carcinoma F3II cells by the administration of a synthetic inhibitor of the profibrinolytic enzyme urokinase during the early stages of the metastatic core formation (D. F. Alonso, E. F. Farías, V. Ladeda, L. Davel, P. Puricelli, E. Bal de Kier Joffé, Effects of Synthetic Urokinase Inhibitors on Local Invasion and Metastatic Dissemination in a Murine Mammary Tumor Model, Breast Cancer Res. & Treat. 1996, 40:209–33).

As opposed to this, it is known that desmopressin induces a fast and strong increase in the plasma levels of the plasminogen tissue activator, the main effector of endogenous fibrinolysis (A. M. A. Gader, J. Da Costa, J. D. Cash, A New Vasopressin Analogue and Fibrinolysis, Lancet 1973, ii:1417–18; P. M. Mannucci, M. Aberg, I. M. Nilsson, B. Robertson, Mechanism of Plasminogen Activator and Factor VIII Increase after Vasoactive Drugs, Br. J. Haematol. 1975, 30:81–93). Thus, desmopressin would contribute in the dissolution of the fibrin protector "shield" covering circulating tumor cells.

Nevertheless, other complementary actions of desmopressin contributing to its antimetastatic action cannot be excluded. For instance, desmopressin could modify the adhesion of tumor cells by altering P-selectin expression in the vascular endothelium cells (S. Kanwar, R. C. Woodman, M. C. Poon, T. Murohara, A. M. Lefer, K. L. Davenpeck, P. Kubes, Desmopressin Induces Endothelial P-selectin Expression and Leukocyte Rolling in Postcapillary Venules, Blood 1995, 86:2760–66) or blood platelets (T. Wun, T. G. Paglieroni, N. A. Lachant, Desmopressin Stimulates the Expression of P-selectin on Human Platelets In Vitro, J. Lab. Clin. Med. 1995, 126:401–09). Desmopressin could also modify the hemodynamics of the blood flow or induce lysis of metastatic cells through the production of nitric oxide from the vasculature (Y. Yamada, M. Nakayama, H. Nakano, N. Mimura, S. Yoshida, Endothelium-Dependent Vasorelaxation Evoked by Desmopressin and Involvement of Nitric Oxide in Rat Aorta, Am. J. Physiol. 1993, 264:E203–07).

Conventional formulations of desmopressin for the parenteral use are generally presented in 1 ml ampoules with 4 $\mu$g/ml of desmopressin in aqueous solution, including chlorobutanol at a concentration of 5 mg/ml as preservative. This preservative is known to alter platelet aggregation by means of a specific mechanism which would involve the inhibition of the arachidonic acid biochemical route (S. L. Chen, W. C. Yang, T. P. Huang, S. A. Wann, C. M. Teng, Chlorobutanol, a Preservative of Desmopressin, Inhibits Human Platelets Aggregation and Release In Vitro. Thromb. Haemost. 1990, 64:473–77). In view of the platelet involvement in biological mechanisms at stake in the host during transportation of cancer cells in blood and in metastatic colonization, the preparations of desmopressin to be used as an antimetastatic should not include chlorobutanol.

However, we have shown that butanol type alcohols are capable of inhibiting intracellular signals which govern the production of profibrinolytic effectors, also in mammary tumor cells themselves (J. A. Aguirre Ghiso, E. F. Farías, D. M. Fernández, S. Klein, D. F. Alonso, E. Bal de Kier Joffé, Down Modulation of Tumor-Associated Proteolytic Activity by n-Butanol in Cultured Murine Mammary Adenocarcinoma Cells, Int. J. Oncol. 1996, 8:35–39; J. A. Aguirre Ghiso, D. F. Alonso, E. F. Farías, E. Bal de Kier Joffé, Overproduction of Urokinase-Type Plasminogen Activator is Regulated by Phospholipase D- and Protein Kinase C-dependent Pathways in Murine Mammary Adenocarcinoma Cells, Biochim. Biophys. Acta 1997, 1356:171–84). Thus, chlorobutanol could also limit the activation of the fibrinolysis process, one of the main mechanisms accounting for the antimetastatic action of desmopressin.

The new formulation of desmopressin to be used as an antimetastatic in accordance with the present invention, should then be preferably established from the lyophilized peptide or one of its pharmaceutically acceptable salts, which is resuspended in saline at the moment of the i.v. application thereof. Cold-lyophilized desmopressin storage or that of the salts thereof—preferably desmopressin acetate—allows an adequate conservation, thus making the use of the preservative chlorobutanol redundant.

The product can be presented in flask-ampoules containing 25 µg of lyophilized pure desmopressin, in a set comprising 2 or 4 flask-ampoules, with a 50 ml flask or sachet of physiological saline solution (Table 2). At the moment of use, desmopressin shall be resuspended in the physiological solution, in an adequate amount according to the body weight and shall be administered as a slow endovenous infusion.

TABLE 2

| Component | Amount |
| --- | --- |
| Lyophilized pure desmopressin | 25 µg Flask-ampoule |
| Aqueous saline solution, sodium chloride 9 g/l | 50 ml Flask or sachet |

As mentioned above, desmopressin has been used in; the classic formulation, including chlorobutanol, in patients suffering from diabetes insipidus in a variety of coagulation disorders (D. W. Richardson, A. G. Robinson, Desmopressin, Ann.: Intern. Med. 1985, 103:228–39; P. M. Mannucci, Desmopressin, A Nontransfusional Form of Treatment for Congenital and Acquired Bleeding Disorders, Blood 1988, 72:1449–55). Desmopressin is presented as a secure and effective hemostatic agent during surgery in patients with hemophilia or the von Willebrand disease (J. C. Horrow, Desmopressin and Antifibrinolytics, Int. Anesthesiol. Clin. 1990, 28:230–36).

Generally desmopressin administration is well tolerated and exhibits few side effects. A 2 mg/kg dose, about 1,000-fold higher than that used in humans, has shown no relevant effects in mice. Very seldom, it causes transient cephalea, nausea, light abdominal cramps and fatigue. Intravenous administration might lead to a clinical pattern of arterial hypotension. The hyponatremia secondary to the hydric retention by the antidiuretic action of desmopressin does not suggest calling for clinical solutions. No thrombotic complications have been reported in patients affected by a cardiovascular disease and treated with desmopressin; current data reflects that the thrombotic risk only represents 0.0001% (F. Rodeghiero, G. Castaman, P. M. Mannucci, Clinical Indications for Desmopressin (DESMOPRESINA [Spanish term]) in Congenital and Acquired von Willebrand Disease, Blood Rev. 1991, 5:155–61). All in all, it is advisable to avoid the use thereof in people with special thrombotic risk.

After the i.v. administration of desmopressin at a dose lower than 20 µg, the peptide half-life may amount to 160 minutes, while their biologicals actions are held up to 6 hours. Metabolization of desmopressin is produced in the liver and kidneys, 60% of the drug being eliminated unmetabolized (D. W. Richardson, A. G. Robinson, Desmopressin, Ann. Intern. Med. 1985, 103:228–39).

Our assays show the antimetastatic properties of desmopressin, using 0.3 to 4 µg/kg of body weight doses, preferably between 1 and 2 µg/kg. Advantageously, desmopressin doses within these ranges, are well characterized from a pharmacological viewpoint (Mannucci 1988 and Horrow 1990 already mentioned and S. Lethagen, Desmopressin and Hemostasis, Ann. Hematol. 1994, 69:173–80).

Our observations strongly suggest a new clinical application for desmopressin, in a new formulation, during surgical extirpation of breast cancer. The tumoral mass mobilization during surgery produces the release of thousands of cancer cells into the circulation. This fact has been unmistakably confirmed in humans by means of reverse transcription and polymerase chain reaction (RT-PCR) techniques during mammary cancer surgery (Brown et al. 1995). Thus, the adjuvant therapy with desmopressin together with the surgical act hereby proposed will significantly limit the implantation of metastatic cells and will be able to improve prognosis in patients with breast cancer.

It is therefore an object of the invention a method of treatment comprising the administration of desmopressin or a pharmaceutically acceptable salt thereof, in i.v. infusion during the neoplastic mass extirpation surgery. Preferably, the endovenous infusion will be slow and extending from 15 to 30 minutes in correspondence with the manipulation and extirpation of the neoplastic mass themselves. Optionally a second post-operative dose may be applied, administered 24 hours after surgery.

In Table 3 below a preferred approach to the treatment in humans is described:

TABLE 3

| 1st Intra-operative dose | 1–2 µg/kg of body weight of desmopressin, dissolved at the time, in 50–100 ml of 0.9% saline solution are administered in i.v. infusion for 15–30 minutes during surgery, corresponding to the manipulation and extirpation of the neoplastic mass. |
| --- | --- |
| 2nd Post-operative dose | 1–2 µg/kg of body weight of desmopressin, dissolved at the time, in 50–100 ml of 0.9% saline solution are administered in i.v. infusion for 15–30 minutes, 24 hours after surgery. |

Pre-clinic assays presented in this work conclusively show the in vivo antimetastatic properties of desmopressin on mammary carcinomas and adenocarcinomas. However, this action might well be developed on any other malignant solid tumor having metastatic potential and disseminating into the blood circulation. In particular, those carcinomas and adenocarcinomas originating from organs different from the mammary gland, which could also induce peritumoral fibrin deposition and which are subject to a similar intravascular transportation.

We claim:

1. A method of treating a mammal to inhibit metastatic dissemination in a second site by metastatic tumor cell spread during the surgery of a cancerous tumor in a first site using the step of administering during said surgery a pharmaceutical composition comprising a therapeutically effective amount of desmopressin.

2. The method according to claim 1 wherein the pharmaceutical composition of desmopressin is administered at a desmopressin dose ranging from 0.3 to 4 µg/kg of body weight by endovenous infusion during surgery.

3. The method according to claim 1 wherein the pharmaceutical composition of desmopressin is administered at a desmopressin dose ranging from 1 to 2 µg/kg of body weight by endovenous infusion during surgery.

4. The method according to claim 1 wherein the pharmaceutical composition of desmopressin is further administered as a second desmopressin dose ranging from 0.3 to 4 µg/kg of body weight by endovenous infusion 24 hours after surgery.

5. The method according to claim 2 wherein the pharmaceutical composition of desmopressin is further administered as a second desmopressin dose ranging from 0.3 to 4 µg/kg of body weight by endovenous infusion 24 hours after surgery.

6. The method according to claim 3 wherein the pharmaceutical composition of desmopressin is further administered as a second desmopressin dose ranging from 0.3 to 4 µg/kg of body weight by endovenous infusion 24 hours after surgery.

7. The method according to claim 1 wherein the pharmaceutical composition of desmopressin is further administered as a second desmopressin dose ranging from 1 to 2 µg/kg of body weight by endovenous infusion 24 hours after surgery.

8. The method according to claim 2 wherein the pharmaceutical composition of desmopressin is further administered as a second desmopressin dose ranging from 1 to 2 µg/kg of body weight by endovenous infusion 24 hours after surgery.

9. The method according to claim 3 wherein the pharmaceutical composition of desmopressin is further administered as a second desmopressin dose ranging from 1 to 2 µg/kg of body weight by endovenous infusion 24 hours after surgery.

* * * * *

SEQUENCE LISTING

<160> NUMBER OF SEQ ID NOS: 2

<210> SEQ ID NO 1
<211> LENGTH: 5
<212> TYPE: PRT

```
<213> ORGANISM: Mammals

<400> SEQUENCE: 1

Gly Arg Gly Asp Ser
1               5

<210> SEQ ID NO 2
<211> LENGTH: 9
<212> TYPE: PRT
<213> ORGANISM: Mammals

<400> SEQUENCE: 2

Cys Tyr Phe Glu Asp Cys Pro Arg Gly
1               5
```